US009524424B2

(12) United States Patent
Greene

(10) Patent No.: US 9,524,424 B2
(45) Date of Patent: Dec. 20, 2016

(54) CALCULATION OF MINIMUM GROUND CLEARANCE USING BODY WORN SENSORS

(75) Inventor: Barry R. Greene, Dublin (IE)

(73) Assignee: CARE INNOVATIONS, LLC, Roseville, CA (US)

( * ) Notice: Subject to any disclaimer, the term of this patent is extended or adjusted under 35 U.S.C. 154(b) by 548 days.

(21) Appl. No.: 13/223,759

(22) Filed: Sep. 1, 2011

(65) Prior Publication Data
US 2013/0060512 A1    Mar. 7, 2013

(51) Int. Cl.
G06K 9/00    (2006.01)
A61B 5/11    (2006.01)
G06F 19/00   (2011.01)
A61B 5/00    (2006.01)
A61B 5/103   (2006.01)

(52) U.S. Cl.
CPC ........... *G06K 9/00342* (2013.01); *A61B 5/112* (2013.01); *A61B 5/1121* (2013.01); *G06K 9/00563* (2013.01); *A61B 5/1036* (2013.01); *A61B 5/1127* (2013.01); *A61B 5/7285* (2013.01); *G06F 19/3437* (2013.01)

(58) Field of Classification Search
CPC ...................................... A61B 5/112
See application file for complete search history.

(56) References Cited

U.S. PATENT DOCUMENTS

| 3,791,375 A | 2/1974 | Pfeiffer |
| 4,738,269 A | 4/1988 | Nashner |
| 5,052,406 A | 10/1991 | Nashner |
| 5,209,240 A | 5/1993 | Jain |
| RE34,663 E | 7/1994 | Seale |
| 5,388,591 A | 2/1995 | De Luca et al. |
| 5,919,149 A | 7/1999 | Allum |
| 6,059,576 A | 5/2000 | Brann |
| 6,063,046 A | 5/2000 | Allum |

(Continued)

FOREIGN PATENT DOCUMENTS

| WO | 2011002788 A2 | 1/2011 |
| WO | 2011016782 A1 | 2/2011 |
| WO | 2012094486 A1 | 7/2012 |

OTHER PUBLICATIONS

McGrath et al., Estimation of minimum ground clearance using body-worn inertial sensors, Journal of Biomechanics, Apr. 7, 2011.*

(Continued)

*Primary Examiner* — Gregory J Toatley
*Assistant Examiner* — Kyle R Quigley
(74) *Attorney, Agent, or Firm* — Pillsbury Winthrop Shaw Pittman LLP

(57) ABSTRACT

Methods, systems, and apparatus for deriving a relationship between minimum ground clearance (MGC) and inertial sensor data. A regression model may be generated by collecting tri-axial angular velocity and acceleration data from inertial sensors and MGC data from optical motion capture systems during a walking trial. A linear, quadratic, interaction, stepwise interaction, or another regression model may be generated. The regression model may estimate the MGC as a function of one or more parameters measured by or derived from the inertial sensor data. The regression model may be used to calculate an estimate of the MGC based on inertial sensor data collected from one or more individuals.

19 Claims, 13 Drawing Sheets

(56) References Cited

U.S. PATENT DOCUMENTS

| | | | |
|---|---|---|---|
| 6,820,025 | B2 | 11/2004 | Bachmann et al. |
| 6,852,086 | B2 | 2/2005 | Atlas et al. |
| 7,141,026 | B2 | 11/2006 | Arminian et al. |
| 7,361,150 | B2 | 4/2008 | Berthonnaud |
| 7,526,071 | B2 | 4/2009 | Drapeau |
| 7,998,092 | B2 | 8/2011 | Avni et al. |
| 8,011,229 | B2 | 9/2011 | Lieberman et al. |
| 8,092,355 | B2 | 1/2012 | Mortimer |
| 8,109,590 | B2 | 2/2012 | Shibata |
| 8,152,744 | B2 | 4/2012 | Mukumoto |
| 8,261,611 | B2 | 9/2012 | Kim et al. |
| 8,280,681 | B2 | 10/2012 | Vock et al. |
| 8,308,665 | B2 | 11/2012 | Harry et al. |
| 8,405,510 | B2 | 3/2013 | Shieh |
| 8,529,448 | B2 | 9/2013 | McNair |
| 8,823,526 | B2 | 9/2014 | Kaiser et al. |
| 8,852,128 | B2 | 10/2014 | Bhattacharya |
| 8,961,439 | B2 | 2/2015 | Yang et al. |
| 8,990,041 | B2 | 3/2015 | Grabiner et al. |
| 2001/0053883 | A1 | 12/2001 | Yoshimura et al. |
| 2002/0077567 | A1 | 6/2002 | McLeod |
| 2004/0143452 | A1 | 7/2004 | Pattillo et al. |
| 2005/0010139 | A1 | 1/2005 | Aminian et al. |
| 2005/0182341 | A1 | 8/2005 | Katayama et al. |
| 2006/0166737 | A1 | 7/2006 | Bentley |
| 2006/0282017 | A1 | 12/2006 | Avni et al. |
| 2007/0057786 | A1 | 3/2007 | McClure et al. |
| 2007/0118043 | A1 | 5/2007 | Oliver et al. |
| 2008/0146968 | A1 | 6/2008 | Hanawaka et al. |
| 2008/0167580 | A1 | 7/2008 | Avni et al. |
| 2008/0243265 | A1 | 10/2008 | Lanier et al. |
| 2008/0281550 | A1* | 11/2008 | Hogle et al. ............... 702/127 |
| 2008/0306410 | A1 | 12/2008 | Kalpaxis et al. |
| 2009/0076419 | A1 | 3/2009 | Namineni et al. |
| 2009/0076765 | A1 | 3/2009 | Kulach et al. |
| 2009/0185772 | A1 | 7/2009 | Xia et al. |
| 2009/0196206 | A1 | 8/2009 | Weaver et al. |
| 2009/0216156 | A1 | 8/2009 | Lengsfeld et al. |
| 2009/0240170 | A1 | 9/2009 | Rowley |
| 2009/0247909 | A1 | 10/2009 | Mukumoto |
| 2009/0247910 | A1 | 10/2009 | Klapper |
| 2009/0260426 | A1 | 10/2009 | Lieberman et al. |
| 2009/0318779 | A1 | 12/2009 | Tran |
| 2010/0152622 | A1 | 6/2010 | Teulings |
| 2011/0022349 | A1 | 1/2011 | Stirling |
| 2011/0092860 | A1 | 4/2011 | Salarian et al. |
| 2011/0118620 | A1 | 5/2011 | Scheib |
| 2011/0119267 | A1 | 5/2011 | Forman et al. |
| 2011/0162433 | A1 | 7/2011 | Peng et al. |
| 2011/0184225 | A1 | 7/2011 | Whitall et al. |
| 2011/0190593 | A1 | 8/2011 | McNair |
| 2011/0190667 | A1 | 8/2011 | Alwan |
| 2011/0213278 | A1 | 9/2011 | Horak |
| 2011/0264010 | A1 | 10/2011 | Williams |
| 2011/0275956 | A1 | 11/2011 | Son et al. |
| 2011/0288811 | A1 | 11/2011 | Greene |
| 2012/0021873 | A1 | 1/2012 | Brunner |
| 2012/0059282 | A1 | 3/2012 | Agichtein et al. |
| 2012/0065915 | A1 | 3/2012 | Hara et al. |
| 2012/0072168 | A1 | 3/2012 | Yin et al. |
| 2012/0092169 | A1 | 4/2012 | Kaiser et al. |
| 2012/0101411 | A1 | 4/2012 | Hausdorff et al. |
| 2012/0119904 | A1* | 5/2012 | Coleman Boone et al. ............ 340/539.12 |
| 2012/0198949 | A1 | 8/2012 | Xia et al. |
| 2012/0232430 | A1 | 9/2012 | Boissy |
| 2012/0253234 | A1 | 10/2012 | Yang et al. |
| 2012/0289791 | A1 | 11/2012 | Jain et al. |
| 2012/0316843 | A1 | 12/2012 | Beno et al. |
| 2013/0060512 | A1 | 3/2013 | Greene |
| 2013/0123665 | A1* | 5/2013 | Mariani et al. ............... 600/592 |
| 2013/0123666 | A1 | 5/2013 | Giuffrida et al. |
| 2013/0123669 | A1 | 5/2013 | Kinoshita et al. |
| 2013/0218053 | A1 | 8/2013 | Kaiser et al. |
| 2013/0303860 | A1 | 11/2013 | Bender |

OTHER PUBLICATIONS

Greene et al., An adaptive gyroscope-based algorithm for temporal gait analysis, Med Biol Eng Comput, Sep. 2, 2010.*
Greene et al., Quantitative Falls Risk Assessment Using the Timed Up and Go Test, IEEE, Dec. 2010.*
O'Donovan et al., Shimmer A new tool for temporal Gait analysis, IEEE, Sep. 3, 2009.*
Lai, A hybrid Support Vector Machine and autoregressive model for detecting gait disorders in the elderly, IEEE, 2007.*
Macon State College, Quadratic Regression, 2007.*
Greene, Barry R. et al., Assessment of Cognitive Decline Through Quantitative Analysis of the Timed Up and Go Test, IEEE Transactions on Biomedical Engineering, vol. 59, No. 4, Apr. 2012, pp. 988-995.
Greene, Barry R, et al., Body-worn sensor based surrogates of minimum ground clearance in elderly fellers and controls, 33rd Annual International Conference of the IEEE EMBS, Boston, Massachusetts USA, Aug. 30-Sep. 3, 2011.
Greene, Barry R. et al., Adaptive estimation of temporal gait parameters using body-worn gyroscopes, 32nd Annual International Conference of the IEEE EMBS, Buenos Aires, Argentina, Aug. 31-Sep. 4, 2010.
Greene, Barry R. et al., Falls risk assessment through quantitative analysis of TUG, Mar. 21, 2010.
Doheny, Emer P., et al., A single gyroscope method for spatial gait analysis, 32nd Annual International Conference of the IEEE EMBS, Buenos Aires, Argentina, Aug. 31-Sep. 4, 2010.
Brach, Jennifer S., et al., "Gait Variability and the Risk of Incident Mobility Disability in Community Dwelling Older Adults," 2007, Journal of Gerontology: Medical Sciences, vol. 62A, No. 9, pp. 983-988.
Deshpande et al., "Gait speed under varied challenges and cognitive decline in older persons: a prospective study," Jul. 25, 2009, Oxford University Press on behalf of the British Geriatrics Society, pp. 509-514.
Doheny, Emer P., et al., "An Instrumented sit-to-stand test used to examine differences between older fallers and non-fallers," Aug. 30-Sep. 3, 2011; IEEE EMBS; 33rd Annual Conference, pp. 3063-3066.
Extended European Search Report issued Dec. 12, 2014 in European Application 13177482.0.
Ferraris et al., "Procedure for Effortless In-Field Calibration of Three-Axis Rate Gyros and Acelerometers," Sensors and Materials, vol. 7, No. 5, 1995, pp. 311-330.
Foroughi, H. et al., "Robust Fall Detection Using Human Shape and Multi-class Support Vector Machine", Sixth Indian Conference on Computer Vision, Graphics & Image Processing, pp. 413-420, ISBN: 978-0-7695-3476-3, XP 031409478, Dec. 16, 2008.
Fried et al., "Frailty in Older Adults: Evidence for a Phenotype," Journal of Gernatology: Medical Sciences, 2001, vol. 56A, No. 3, pp. M146-M156.
Friedman, Jerome H., "Regularized Discriminant Analysis," Jul. 1988, Journal of the American Statistical Association, pp. 1-32.
Giansanti, "Assessment of fall-risk by means of a neural network based on parameters assessed by a wearable device during posturography", Medical Engineering & Physics, vol. 30, 2008, pp. 367-372.
Giansanti, "Investigation of fall-risk using a wearable device with accelerometers and rate gyroscopes", Physiol. Meas, vol. 27, Sep. 11, 2006, pp. 1081-1090.
Gkalelis et al., "Human Movement Recognition Using Fuzzy Clustering and Discrmininant Analysis," Aug. 2008, EUSIPCO.
Greene et al., Classifier Models and Architectures for EEG-Based Neonatal Seizure Detection, Physiol. Meas., 2008, pp. 1157-1178, 29, IOP Publishing, UK.
Greene et al., "Evaluation of Falls Risk in Community-Dwelling Older Adults Using Body-Worn Sensors," Regenerative and Technological Section/Original Paper, Gerontology 2012, vol. 59, pp. 472-480, along with supplementary table.
Greene et al., "Quantatative falls risk estimation through multisensor assessment of standing balance," Physiological Measurement, Physiol. Meas. 33 (2012), pp. 2049-2063.

(56) References Cited

OTHER PUBLICATIONS

Higashi, Yuji et al., "Quantitative Evaluation of Movement Using the Timed-Up-and-Go Test", IEEE Engineering in Medicine and Biology Magazine, Jul./Aug. 2008, pp. 38-46.

International Search Report and Written Opinion mailed Oct. 12, 2011, for PCT/US2011/036955.

Latt, Mark D., et al., "Clinincal and Physiological Assessments for Elucidating Falls Risk in Parkinson's Disease," No. 9, 2009, Movement Disorder Society, vol. 24, pp. 1280-1289.

Makary, M. A., et al., "Frailty as a Predictor of Surgical Outcomes in Older Patients," pp. 901-908, 2010.

Najafi et al., "Measurement of Stand-Sit and Sit-Stand Transitions Using a Miniature Gyroscope and Its Application in Fall Risk Evaluation in the Elderly," Aug. 2002, IEEE Transactions on Biomedical Engineering, vol. 49, No. 8.

Narayanan et al., "Longitudinal Falls Risk Estimation using Triaxial Accelerometry", IEEE Trans., vol. X, No. Y, Jul. 2009, pp. 1-8.

Pavel, Misha, "Continuous Assessment of Gait Velocity in Parkinson's Disease from Unobtrusive Measurements", 2007, 4 pages.

Pavel, Misha, "Unobtrusive Assessment of Mobility", 2006, 5 pages.

Sabatini, A. et al., "Assessment of Walking Features From Foot Inertial Sensing," IEEE Transactions on Biomedical Engineering [online], Mar. 2005 [retrieved on May 17, 2015]. Retrieved from the Internet: <http://ieeexplore.ieee.org/xpls/abs_all.jsp?arnumber=1396389>.

Salarian et al., "iTUG, a Sensitive and Reliable Measure of Mobility", IEEE Transactions on Neural Systems and Rehabilitation Engineering 2010, pp. 1-8.

Vellas et al., "One-Leg Balance is an Important Predictor of Injurious Falls in Older Persons," 1997, American Geriatrics Society, pp. 735-738.

Walsh et al., "Development and Validation of a Clinic Based Balance Assessment Technology," 33rd Annual International Conference of the IEEE EMBS, Aug. 30-Sep. 3, 2011, pp. 1327-1330.

Weiss et al., "Can an accelerometer enhance the utility of the Timed Up & Go Test when evaluating patients with Parkinson's disease?", Medical Engineering & Physics vol. 32, 2010, pp. 119-125.

Zampieri et al., The instrumented timed up and go test: potential outcome measure for disease modifying therapies in Parkinson's disease, Journal Neurology Neurosurgery and Psychiatry, Feb. 1, 2010, pp. 171-176, vol. 81, No. 2.

\* cited by examiner

CALCULATION OF MINIMUM GROUND CLEARANCE USING BODY WORN SENSORS

TECHNICAL FIELD

Embodiments generally relate to falls risk assessment, cognitive decline assessment, and gait analysis. More particularly, embodiments relate to calculation of a walking person's minimum ground clearance (MGC) and general risk of falling based on data collected by inertial sensors.

BACKGROUND

Falls in the elderly may represent a substantial healthcare problem worldwide. Indeed, a significant percentage of people over seventy years of age experience a significant fall, and the frequency of falls increases with age and the level of frailty.

Increased frailty and declining balance may be reflected in how a person walks. The task of walking is a complex motor control challenge, where the human neuromuscular system is required to interact with the environment while maintaining balance during forward momentum. A person must maintain a safe foot trajectory with respect to the ground. Foot trajectory during the swing phase of a person's gait can be sensitive to small angular changes at six other joints within both stance and swing limbs. The sensitivity suggests that foot trajectory involves precise end-point control task. Disturbance of this end-point control may lead to falls or other unprovoked collisions with the ground.

One falls-related parameter measured during walking trials is minimum ground clearance (MGC), which has also been called minimum toe clearance (MTC). The parameter generally reflects how much the walking trial participant lifts his or her foot from the ground during a walk. The MGC may be measured in a specialized gait clinic that uses marker-based optical motion capture systems. The specialized optical motion capture equipment may be operated by specialized personnel to analyze the MGC of the participant.

SUMMARY OF THE INVENTION

One aspect of this invention relates to calculating a minimum ground clearance (MGC) of a person by using data acquired from inertial sensors mounted on the person. Inertial sensors may include accelerometers and gyroscopes, and may be mounted on the person's shanks, feet, or any other part on the person's lower limbs. The inertial sensors may be used as an alternative measurement method to an optical motion capture system, which may be non-portable, expensive, inconvenient to use, and require specialized personnel to operate.

The unit axes of the attached inertial sensors may be oriented so that they align with certain axes or planes defined by the person's body. For example, the sensor's gyroscope Y-axis may be oriented to capture movement in the person's anatomical sagittal plane. The sensor's gyroscope X-axis may be oriented to capture movement about a plane perpendicular to the long line of the shank. The sensor's gyroscope Z-axis may be oriented to measure movement in the plane in which the long line of the shank lies.

Calculation of MGC from the inertial sensor data may be based on predetermined regression models. The predetermined regression models may have been generated from a previous walking trial in which inertial sensor data and reference MGC values were both captured from a walking trial participant. The reference MGC values may have been captured by an optical motion capture system, and constitute values that the regression models need to approximate from the inertial sensor data. After the regression models are generated, a person's MGC may be calculated without using an optical motion capture system. Instead, the regression models may output MGC calculations based on just inertial sensor data input. This calculation thus increases the convenience, portability, and affordability of estimating a person's MGC (or a parameter derived from the MGC).

Among the MGC parameters that may be estimated is the mean MGC and the coefficient of variation (CV) of the MGC. A CV MGC may be used to represent variability of MGC. For example, an estimate of the CV of MGC may be calculated to assess a risk of falling in an elderly person. Elderly men have been found to exhibit greater MGC variability than young men, which suggests that CV MGC may be an important parameter in evaluating increased risk of tripping in the elderly.

Inertial sensor data for generating a regression model may include angular velocity measurements, acceleration measurements, and/or other parameters derived from those measurements, such as the mean absolute-valued vertical angular velocity. The regression model may be generated based on sensor data from a particular person, and may further be generated based on sensor data from a particular body segment, such as a left shank or a left foot.

The inertial sensor data may further be used to directly distinguish between a person with a high risk of falling versus a person with a low risk of falling. For example, mean angular velocity at mid-swing points of a walk, mean absolute-valued angular velocity, and minimum angular velocity may have a different statistical distribution for fallers versus non-fallers. The three angular velocity parameters collected from a person may thus be used to assess whether that person is more likely to be a faller or a non-faller. Other inertial sensor parameters for distinguishing fallers from non-fallers may be identified by correlating the parameters with clinical measures of falls risk. For example, the person generating inertial sensor data may also perform a TUG or BBS test. Inertial sensor parameters that correlate well that person's TUG time or BBS score may be used as a parameter for assessing falls risk. An accurate automated assessment of a risk of falling would allow for timely intervention and therapy to reduce that risk.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

One aspect of this invention is directed toward relating measurements collected from inertial sensors during a walking trial (or any other gait analysis context) and parameters derived from those measurements to a person's minimum ground clearance (MGC). MGC, also called minimum toe clearance (MTC), may be defined as the minimum distance between the foot and the ground during a swing-phase of a gait cycle. At that instant, the foot may be at or near its maximum velocity, the center of mass of the body is outside its base of support, and a small positional error could result in collision with the ground. Thus, low MGC may be a trip hazard and an indication of a risk of falling, such as in the elderly population. Because measuring MGC with an optical motion capture system may require expensive, specialized equipment and personnel, the MGC and MGC parameters, or their estimates, may instead be calculated from parameters measured by or derived from one or more inertial sensors mounted on a person's body, such as his or her feet or legs. The calculation may be based on a regression model that estimates the MGC as a function of the inertial sensor parameters. The regression model may be generated by fitting values of parameters measured by or derived from the inertial sensors to reference MGC values measured by an optical motion capture system. The calculated MGC may be used as part of a falls risk assessment. For example, a statistical model may incorporate the MGC as a parameter to predict an individual's risk of falling.

In some implementations, generation of the regression model and calculation of the MGC may be performed by one or more processors executing one or more instructions stored on a computer-readable medium. The generation of a regression model and calculation of the MGC may also be performed by firmware, logic circuits, and/or any other computing circuit. The computing circuit may also calculate other parameters related to a falls risk assessment. The walking trial in which the inertial sensor data are generated may be part of a gait analysis in which a person's motion is measured while the person is walking a distance (e.g. 15 m or 30 m) in a straight path. The data collected by the inertial sensors may be used to also calculate a gait parameter, such as gait velocity.

Figure 1A:
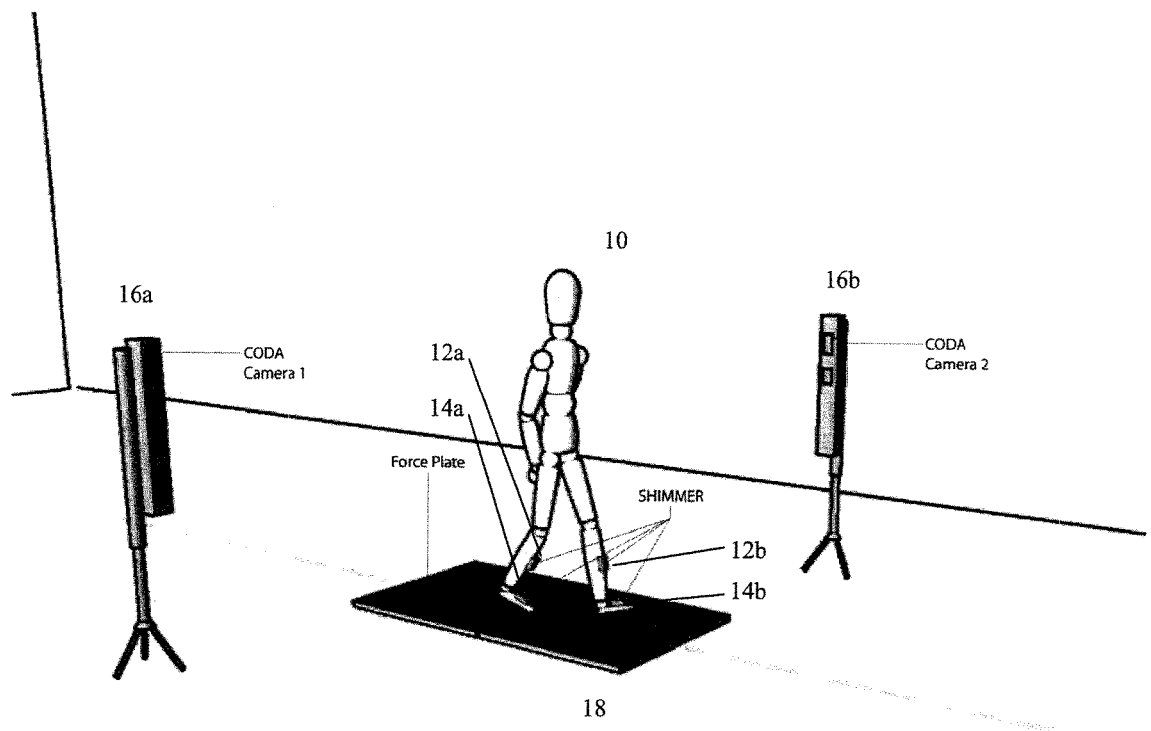
FIG. 1A illustrates a perspective view of an example of an individual performing a walking trial in which inertial sensor data are measured.

FIG. 1A illustrates a walking trial in which inertial sensor parameters and MGC of an individual 10 may be measured.

Figure 1B:
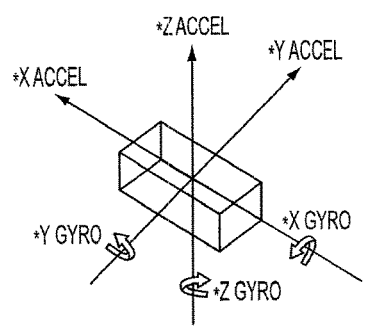
FIG. 1B illustrates a perspective view of an example inertial sensor.

The inertial sensor parameters may be measured by inertial sensors 12a, 12b, 14a, and 14b. In another embodiment, more (e.g., 6) or fewer (e.g., 2) inertial sensors may be used. The embodiment in FIG. 1A shows two sensors, 12a and 12b mounted on the individual's 10 left and right shank and two sensors, 14a and 14b, mounted on the middle of the individual's 10 left feet and right feet. The inertial sensors may include tri-axial accelerometers, tri-axial gyroscopes, GPS transceivers, and any other sensor operable to measure movement or force-related parameters. FIG. 1B shows an example inertial sensor that has an accelerometer and gyroscope. The sensor may measure acceleration and rotation along the sensor's X, Y, Z axes, which may be oriented to align with certain segments of the body. For example, the sensor's gyroscope X-axis may be oriented to capture movement about a plane perpendicular to the long line of the shank, the sensor's gyroscope Y-axis may be oriented to capture movement in the person's anatomical sagittal plane, and the sensor's gyroscope Z-axis may be oriented to measure movement in the plane in which the long line of the shank lies. Inertial sensors such as sensors of the Shimmer™ sensor platform can measure kinematic parameters in real time using, for example, accelerometers, gyroscopes, passive infrared (PIR) sensors, and tilt and vibration sensors. The sensors may be placed at various locations on the body, such as the individual's 10 knees, upper legs, lower legs, or hips. For example, sensors may be attached to the mid-point of the individual 10's anterior shank (i.e., lower leg) by means of tight fitting clothing or elasticized bandages or any other manner of attachment.

In order to ensure that the angular velocity signal derived from the gyroscope has the correct polarity, the "skewness" of the signal (e.g., a measure of the asymmetry of the signal) may be calculated for each walk. If the skewness is less than zero, the gyroscope signal can be inverted to ensure the correct polarity of the signal. The raw gyroscope and accelerometer data may be calibrated to derive the angular velocity and acceleration vectors with respect to sensor unit coordinate axes. A standard calibration procedure may be used to calibrate the gyroscopes before they are used in the walking trial.

Figure 2:
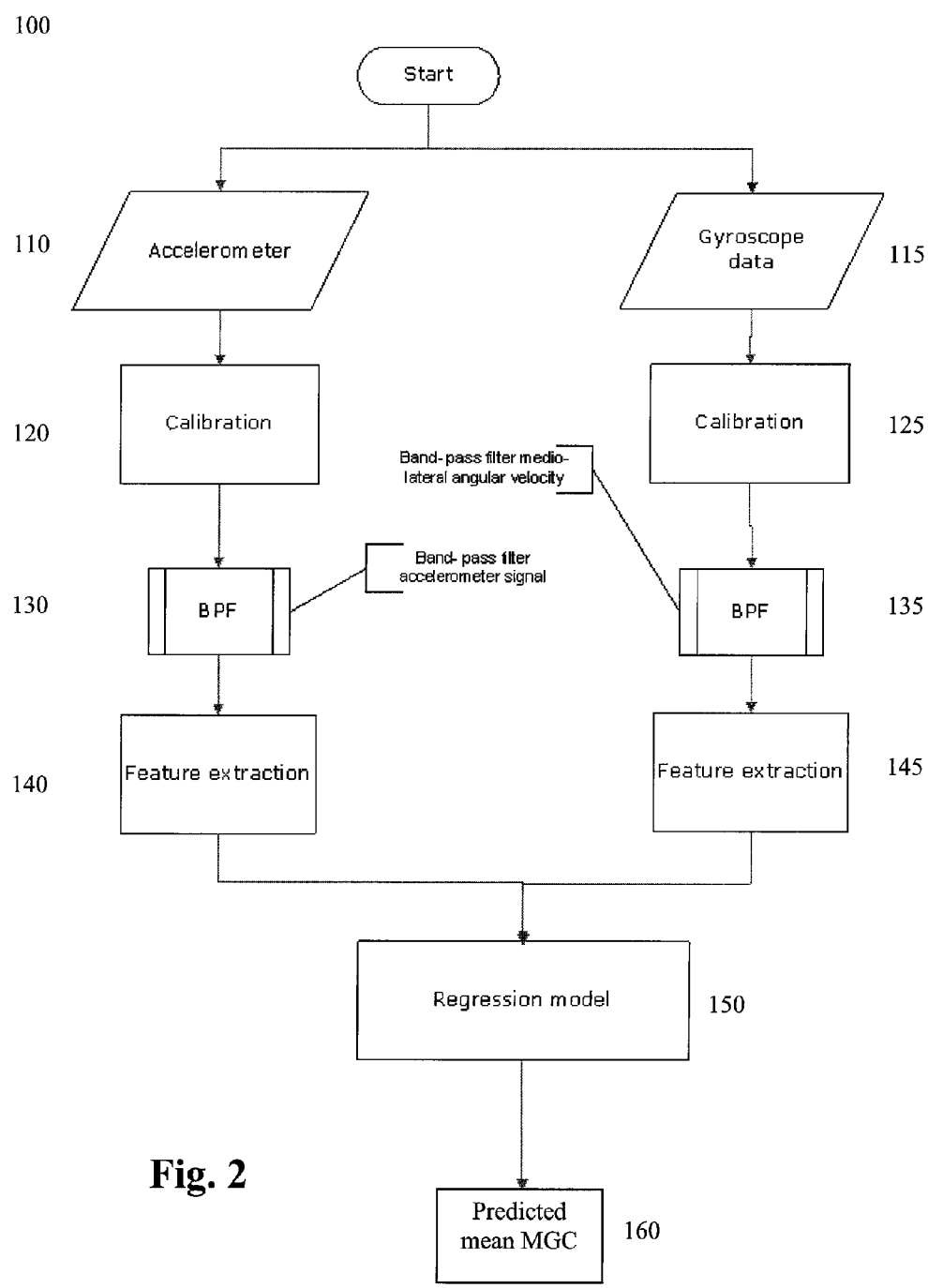
FIG. 2 illustrates example operations of calculation of MGC based on inertial sensor data.

FIG. 2 illustrates example operations 100 of a MGC calculation based on inertial sensor data. At operations 110 and 115, data may be collected from an inertial sensor's accelerometer, gyroscope, or both. The inertial sensors may collect measurements from an individual 10 during a walking trial in which he or she walks at one or more of a variety of speeds. For example, the individual may walk 15 meters at a selected speed, such as slow (e.g., 0.65 m/sec), normal (e.g., 1.1 m/sec), fast (e.g., 1.5 m/sec), or shuffling (e.g., 0.48 m/sec). A shuffling gait may be used to generate inertial sensor data of non-normal gait patterns. Shuffled steps may include the taking of very short, rapid steps, or longer steps in which an individual barely lifts his or her feet off the ground. Inertial sensor data from shuffled steps may represent an aberrant gait pattern and may be used to test whether a model for estimating MGC is robust enough to output an accurate MGC from inertial sensor data associated with a shuffling gait. The speed of the walk may be selected by the individual, to minimize any effects of parameters and protocols of the walking trial on the individual's gait. The inertial sensor data may be collected from individuals walking on a treadmill, or from walking in a more natural context in which the individuals are not influenced by the rhythm of the treadmill. In one example, inertial sensor data may be acquired using four wireless sensors, with one sensor attached to a mid-foot or a shank of the left or right leg of a walking trial participant.

The collection of inertial sensor data and MGC data may be synchronized by using a dedicated trigger output. The trigger output may come from, for example, a force plate 18 placed beneath the individual's feet. The trigger may be connected to the analog-to-digital input of a dedicated synchronization sensor. The synchronization sensor may be made up of, for example, a SHIMMER™ and an Analog Expansion breakout board and may transmit wirelessly to a PC via Bluetooth®, 802.11, or other wireless protocol. The inertial sensor parameters, such as acceleration or angular velocity, may be collected from each axis of the inertial sensors. In one example, the inertial sensor data may be sampled at 102.4 Hz. The data may be transmitted wirelessly from the sensors to a desktop, laptop, server, mobile device, or any other computing device.

At operation 120 and 125, the raw data from the accelerometer and gyroscope, respectively, may be calibrated to derive vertical angular velocity vectors with respect to the sensor unit coordinate axis or some other orientation. In one example, angular velocity may be measured about an axis perpendicular to the sagittal plane of the individual performing the walking trial. In the example, the orientation of the angular velocity may be based on the sagittal plane of the individual 10. The acceleration may be measured in a direction parallel to gravity. At operations 130 and 135, the data may be filtered before or after transmission to remove noise. For example, a zero-phase $5^{th}$ order Butterworth filter with may be used to low pass filter the sensor data. The corner frequency (e.g., 50.2 Hz) may be calculated as $$f_c = \left(\frac{f_s}{2} - 1\right),$$

where $f_s$ is the sampling rate. A bandpass filter may also be used to filter out low-frequency components of the data. The mean, maximum, minimum, range, coefficient of variation, and other statistical parameters may be derived from inertial sensor measurements, such as from angular velocity or acceleration measurements.

Some of the measured or derived inertial sensor parameters (e.g., mean of the absolute values of vertical angular velocity) may be compared to reference MGC measurements, such as from an optical motion capture system that directly measures a person's MGC during a walk. The reference MGC measurements may be used either to generate a regression model that estimates the MGC values from the inertial sensor parameters, or to validate the accuracy of an earlier generated regression model. The reference MGC values may be measured from, for example, an optical motion capture system, such as by CODA (Cartesian Optoelectronic Dynamic Anthropometer) cameras 16a and 16b of a CODA motion capture system. For example, two CODA cx1 units may be used, one placed on either side of the individual 10. Two CODA infrared LED markers may be placed on the left and right foot. In one example, each marker may be placed on the lateral aspect of the fifth metatarsal head of each foot, on the exterior of the individual's shoes. The markers may be placed on other locations on the foot or on other body parts that can be related to MGC. Capture of the optical data may be triggered based on detected movement, or may be initiated at predetermined intervals. For example, the optical data may be sampled at 200 Hz. The minimum vertical displacement of the optical markers may be measured and outputted as the MGC. The measurements may further be adjusted for shoe height to more accurately measure MGC. The measurements may be used as reference or benchmark MGC values that a regression model attempts to approximate with inertial sensor parameters.

A relationship may be derived between data from the inertial sensors and data from the optical capture system so that subsequent measurements collected by the inertial sensors (e.g., angular velocity and acceleration data) may be used to estimate parameters (e.g., MGC) that would otherwise have required the optical motion capture system to measure. The inertial sensor parameters used in generating a model relating the MGC parameter and inertial sensor parameters may differ depend on the MGC parameter (e.g. MGC, mean MGC, CV MGC) being modeled. At operations 140 and 145, feature extraction may be performed to narrow the parameters that need to be used in a regression model. The feature extraction may use techniques such as principal components analysis to determine which parameters measured by or derived from the inertial sensors should be used to model the desired MGC parameter. For example, a regression model for calculating mean MGC may use mean of the absolute values ("mean absolute valued") vertical angular velocity and mean absolute valued acceleration as the input parameters. For example, a regression model for calculating CV MGC may also use mean absolute valued vertical angular velocity, mean absolute valued acceleration, as well as maximum vertical angular velocity, minimum vertical angular velocity, the range of vertical angular velocity, the vertical angular velocity at a mid-swing point, maximum vertical acceleration, minimum vertical acceleration, the range of acceleration, and vertical acceleration at the mid-swing point. The regression model may use inertial sensor data collected from only certain walking trial participants (e.g., based on height or weight), and may further use inertial sensor data collected from certain body segments (e.g., only from foot-mounted inertial sensors). For example, the regression models for both MGC and CV MGC may be generated using the participant number (e.g., 1-9) and leg (left or right) as categorical factors using dummy variables.

Figure 3A:
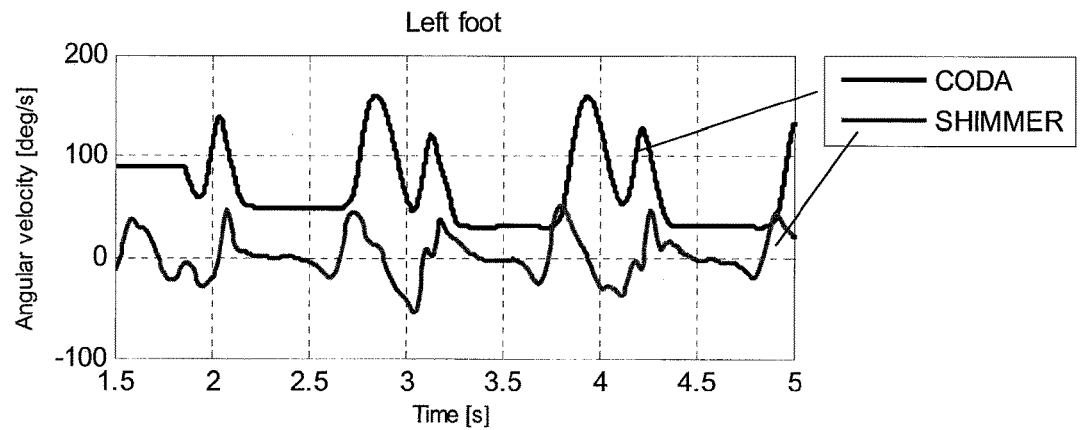
FIG. 3A illustrates example data measured by inertial sensors and by an optical motion capture system.
Figure 3A:
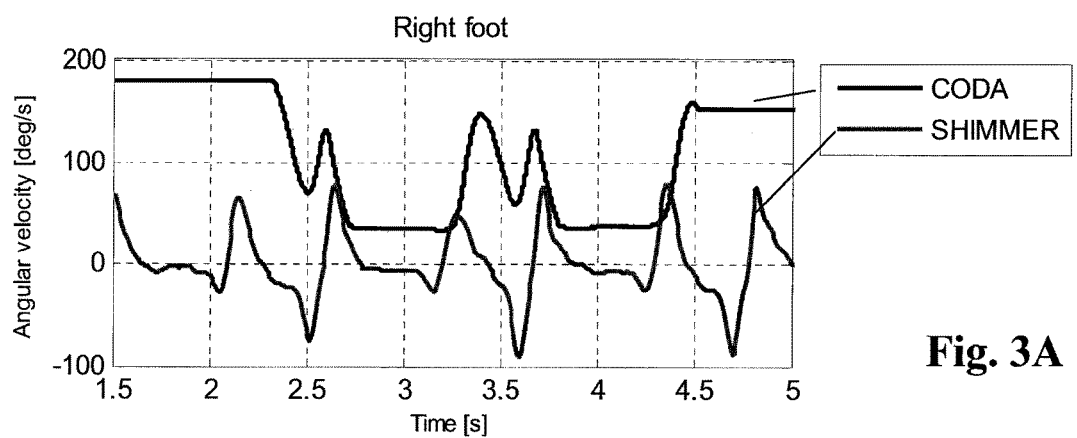

At operation 150, a regression model may be used to relate MGC parameters to inertial sensor parameters. FIG. 3A shows example angular velocity data collected from foot-mounted Shimmer™ sensors and example vertical foot displacement data collected from a CODA optical motion capture system. The two plots indicate that a relationship, such as a linear relationship, may be established between parameters measured by or derived from inertial sensors and MGC parameters. More specifically, vertical displacement of toe marker measured by the optical motion capture system shows concordance with angular velocity (measured about an axis perpendicular to the sagittal plane to relate to the orientation change of the body segment in the sagittal plane) and acceleration (measured in a direction parallel to gravity) signals derived from inertial sensor mounted on a left foot.

In some implementations, a Pearson's Correlation Coefficient may be calculated between the reference MGC or mean MGC values and inertial sensor parameters to find an inertial sensor parameter with a linear relationship to the reference MGC values. Data obtained from a left leg and a right leg may be analyzed separately, to avoid any assumption of gait symmetry (e.g., Pearson's Correlation Coefficient may be higher for data collected from a left foot than from a right foot). In one example, reference optical measurements of mean MGC or coefficient of variation of the MGC (CV MGC) may have a maximum Pearson's Correlation Coefficient (e.g., r=0.77) with the mean vertical angular velocity measured by the inertial sensors. In the example, the mean vertical angular velocity may then be used to generate a linear model that estimates the mean MGC or CV MGC from the mean foot vertical angular velocity.

Figure 3B:
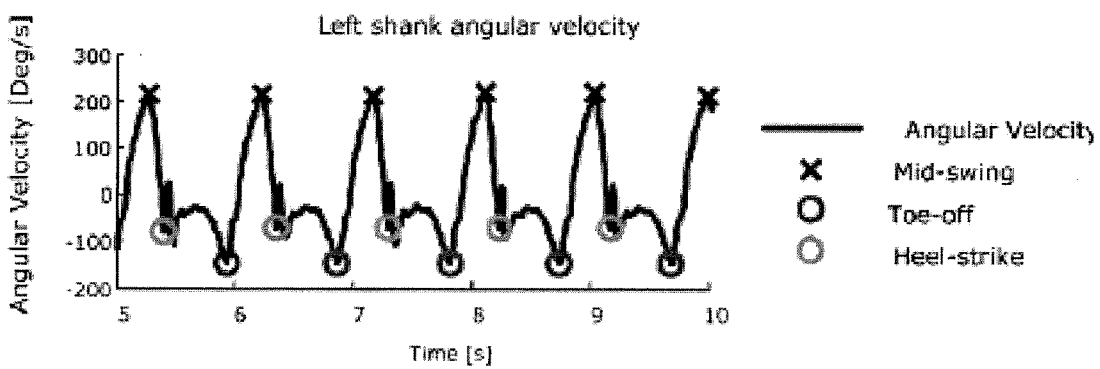
FIG. 3B illustrates example data measured by inertial sensors and example events identified in the data.
Figure 3B:
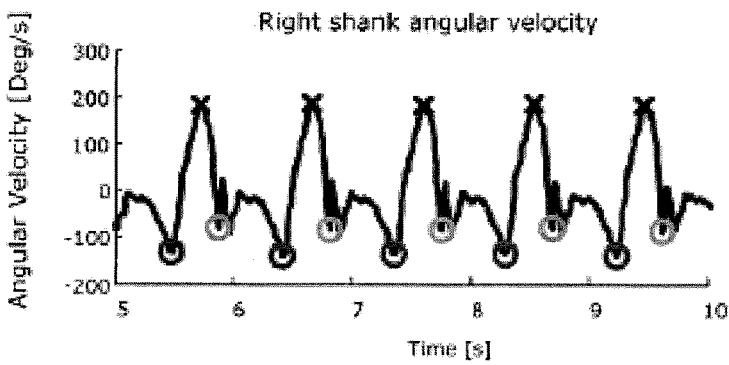

FIG. 3B shows events that may be identified and labeled from the inertial sensors' angular velocity data. For example, FIG. 3B shows that initial contact (i.e. toe-off) points during a walk may be identified as the points where angular velocity is the lowest, and mid-swing points may be identified as the points where angular velocity is the highest. Identifying initial contact (i.e., toe-off) and terminal contact (i.e., heel-strike) points is discussed more in U.S. patent application Ser. No. 12/782,110, entitled "Wireless Sensor Based Quantitative Falls Risk Assessment," the entire content of which is incorporated by reference herein.

Figure 4A:
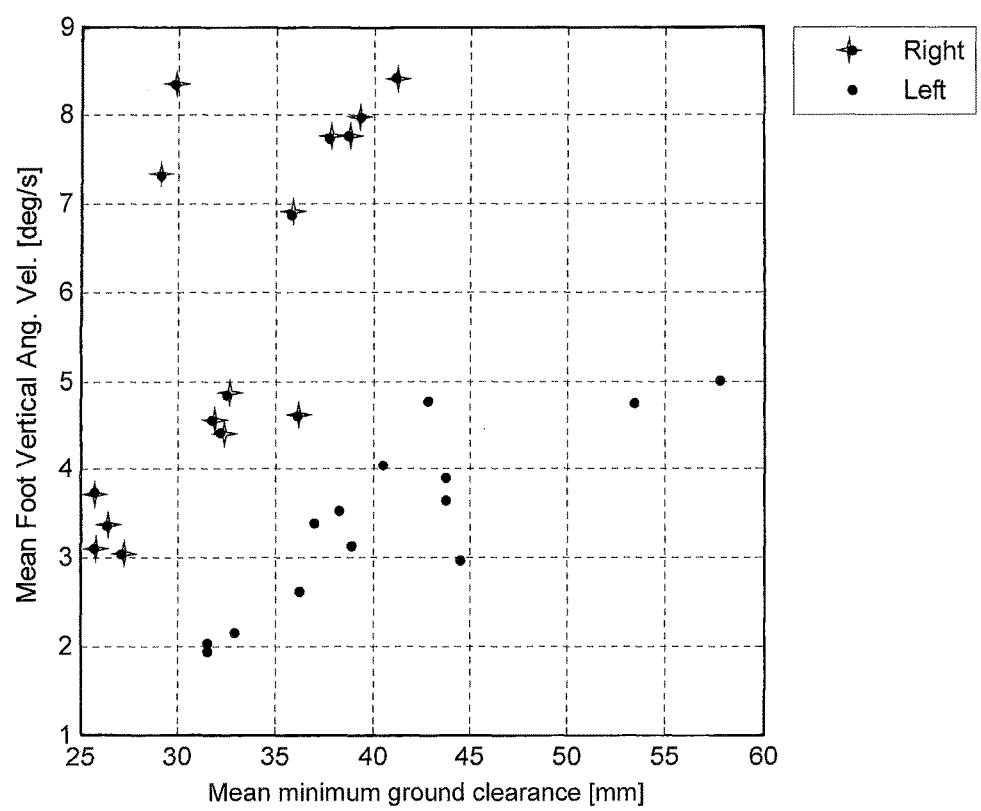
FIGS. 4A-C illustrate example relationships of a MGC parameter to a parameter derived from angular velocity data.
Figure 4B:
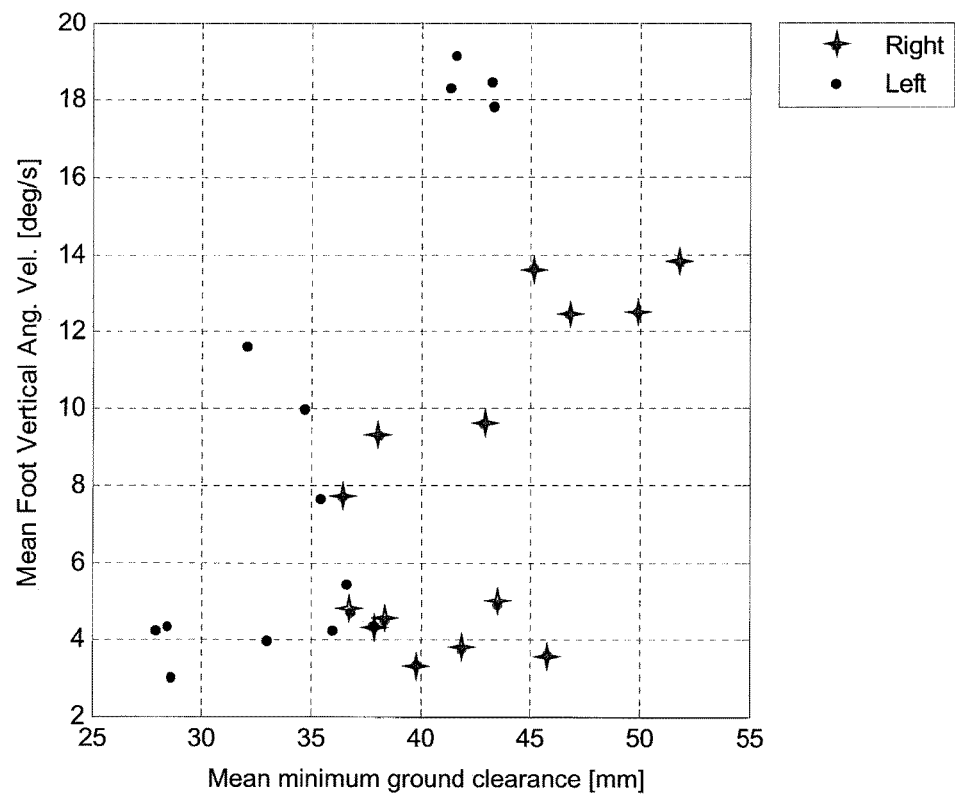
Figure 4C:
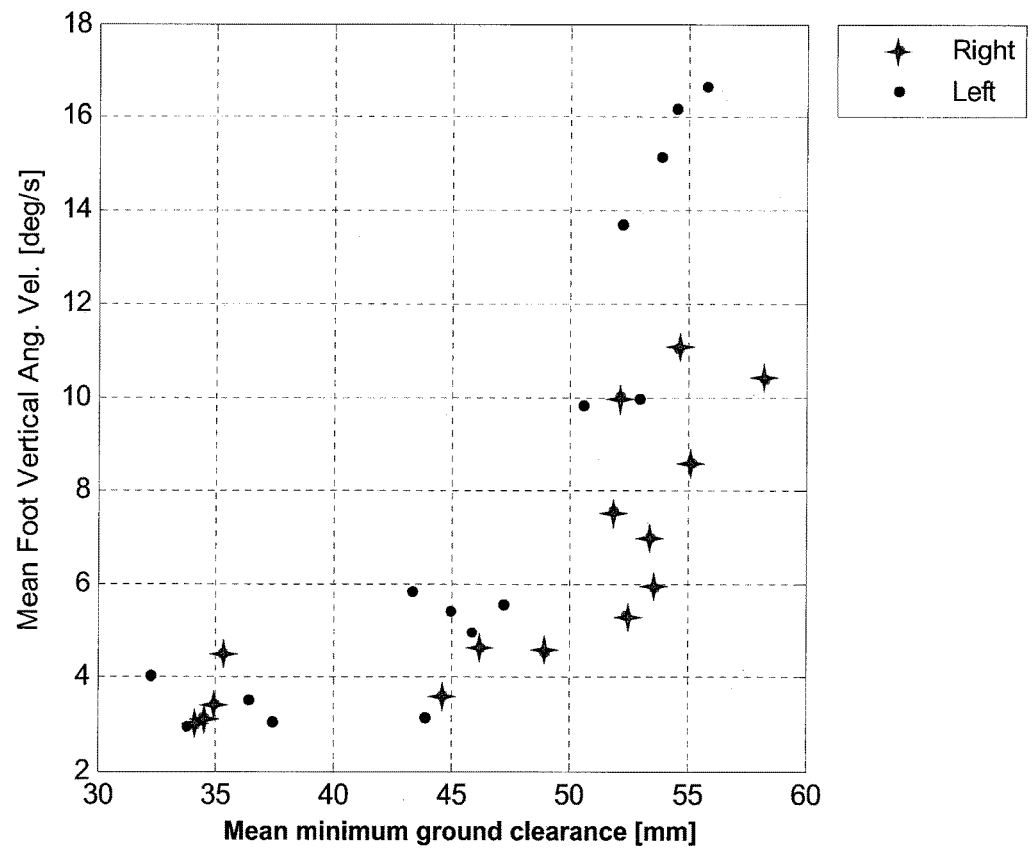

FIGS. 4A-4C illustrate example plots showing approximate relationships between the mean foot vertical angular velocity and the mean MGC. Each plot is based on data generated by a different individual. The data for each individual is divided into that for the left foot and that for the right foot. The data suggests that two separate MGC models for an individual, one based on left foot or left leg inertial sensor parameters and one based on right foot or right leg inertial sensor parameters, may be generated.

Figure 5:
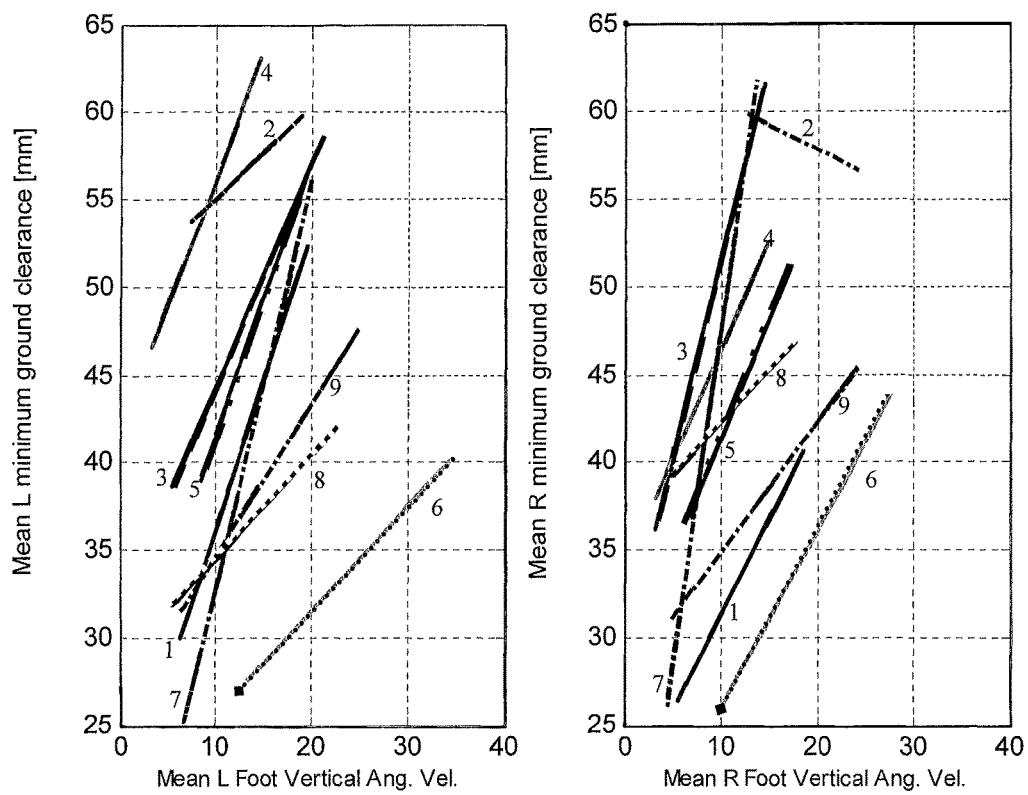
FIG. 5 illustrates example regression models relating a MGC parameter to a parameter derived from angular velocity data.
Figure 6A:
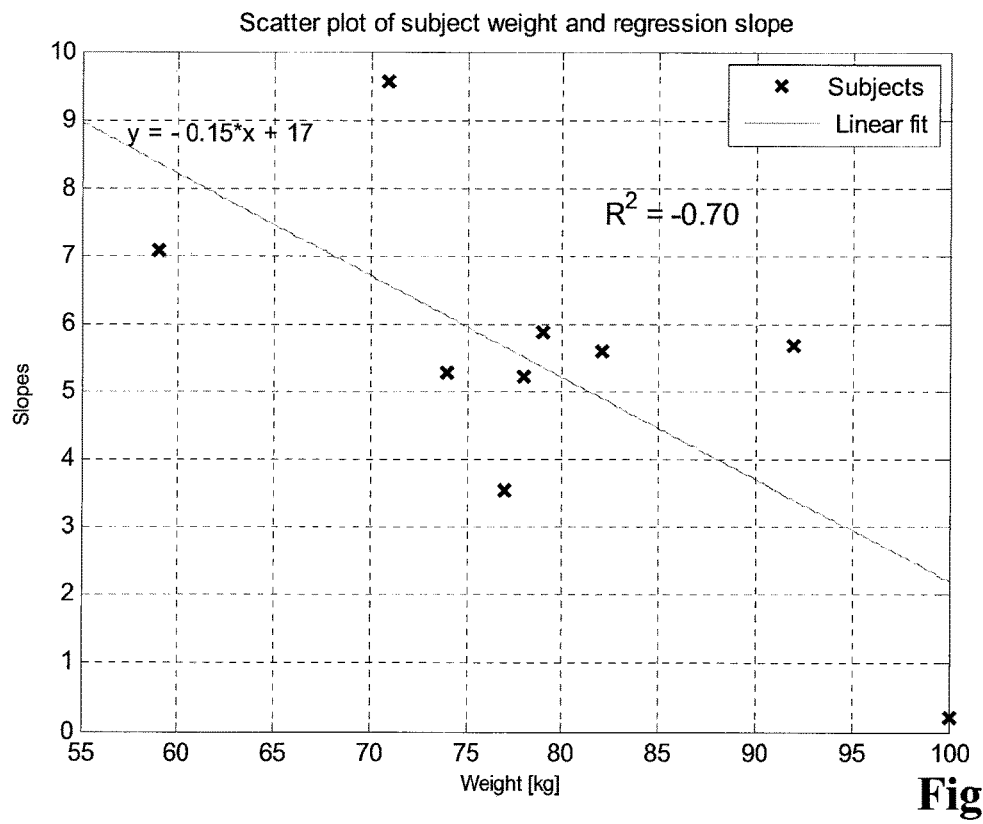
FIG. 6A illustrates example outputs of a linear regression model of a MGC parameter.
Figure 6B:
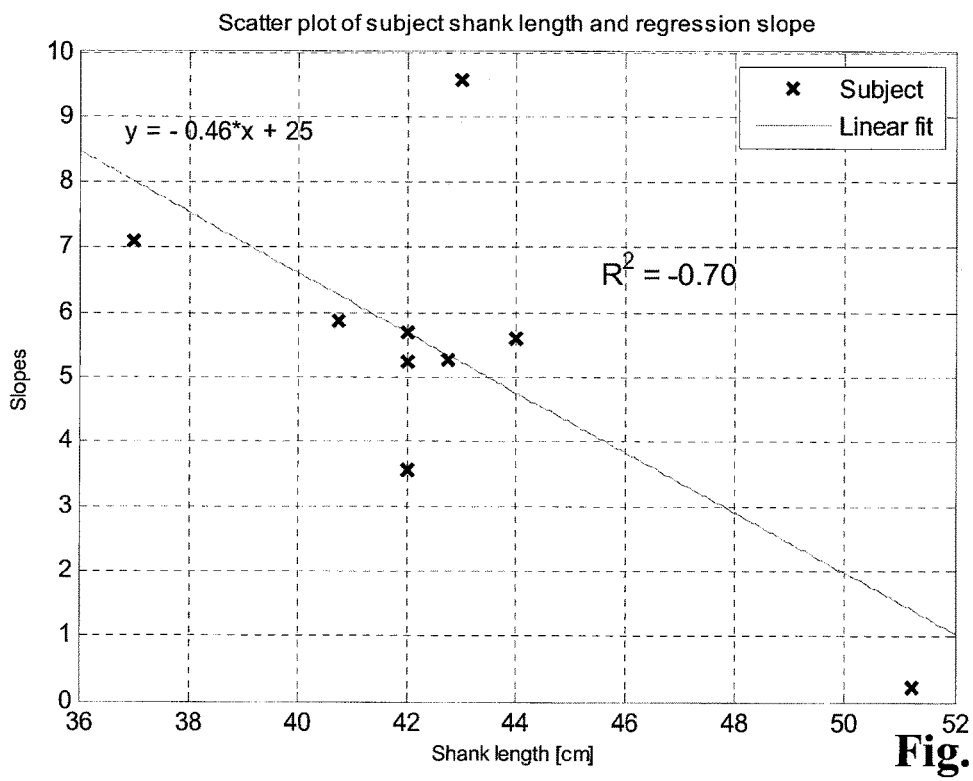
FIG. 6B illustrates example outputs of an interaction regression model of a MGC parameter.
Figure 7A:
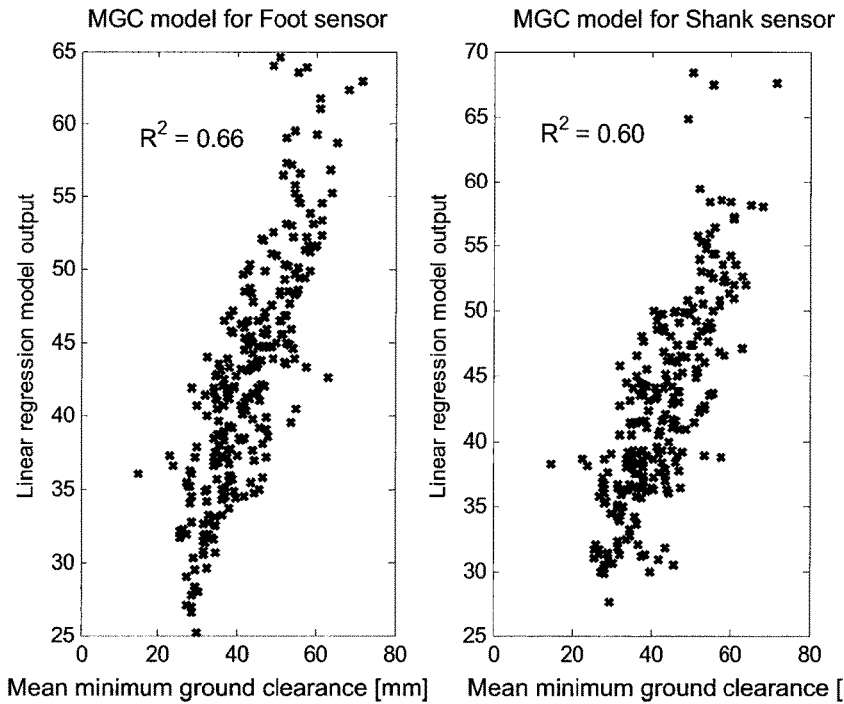
FIG. 7A illustrates example outputs of a linear regression model of a MGC parameter.
Figure 7B:
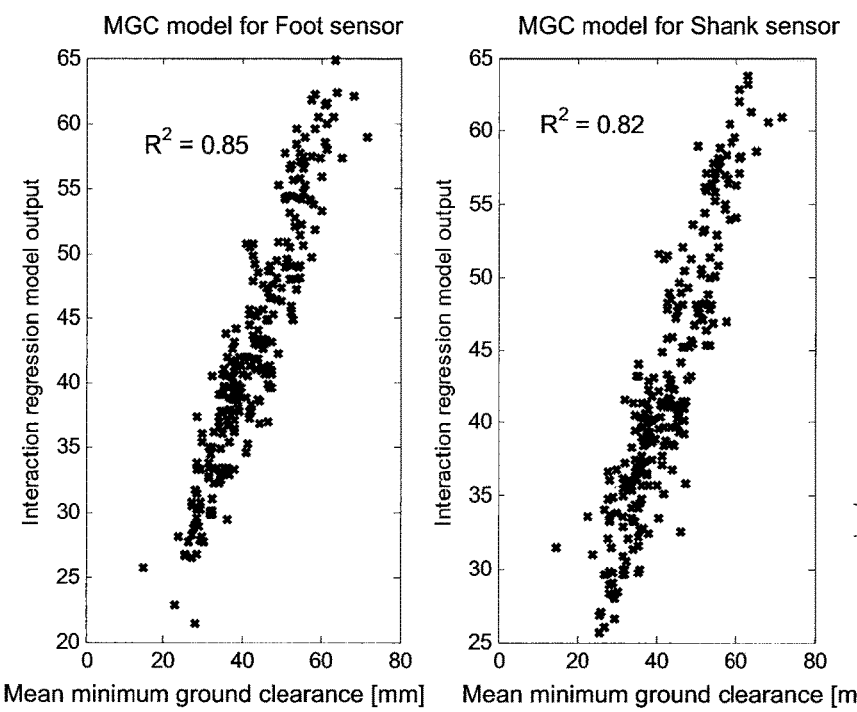
FIG. 7B illustrates example outputs of an interaction regression model of a MGC parameter.
Figure 7C:
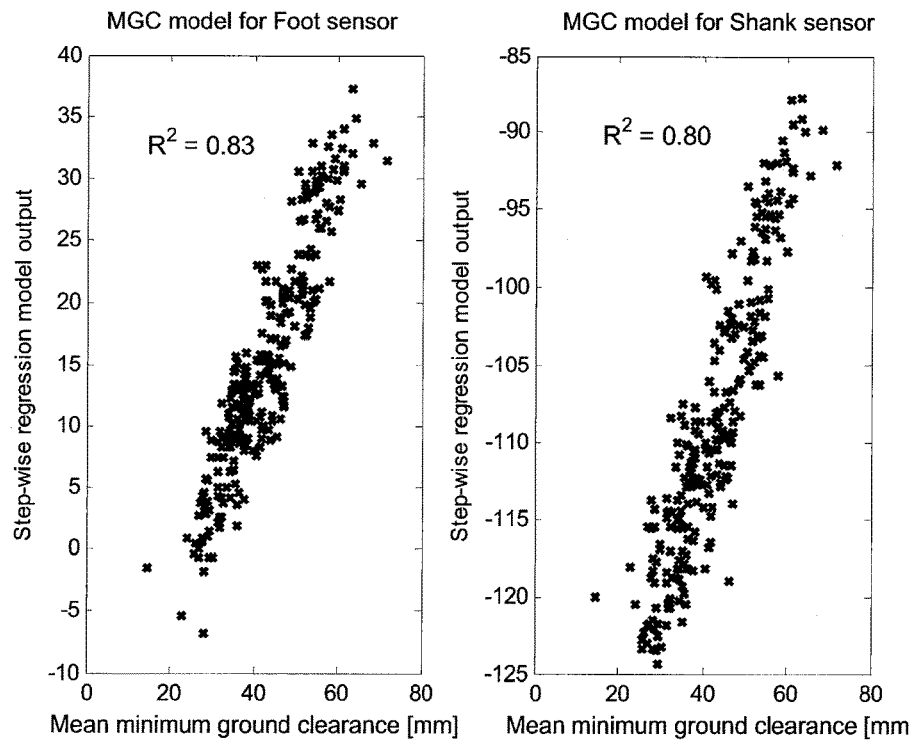
FIG. 7C illustrates example outputs of a stepwise regression model of a MGC parameter.
Figure 7D:
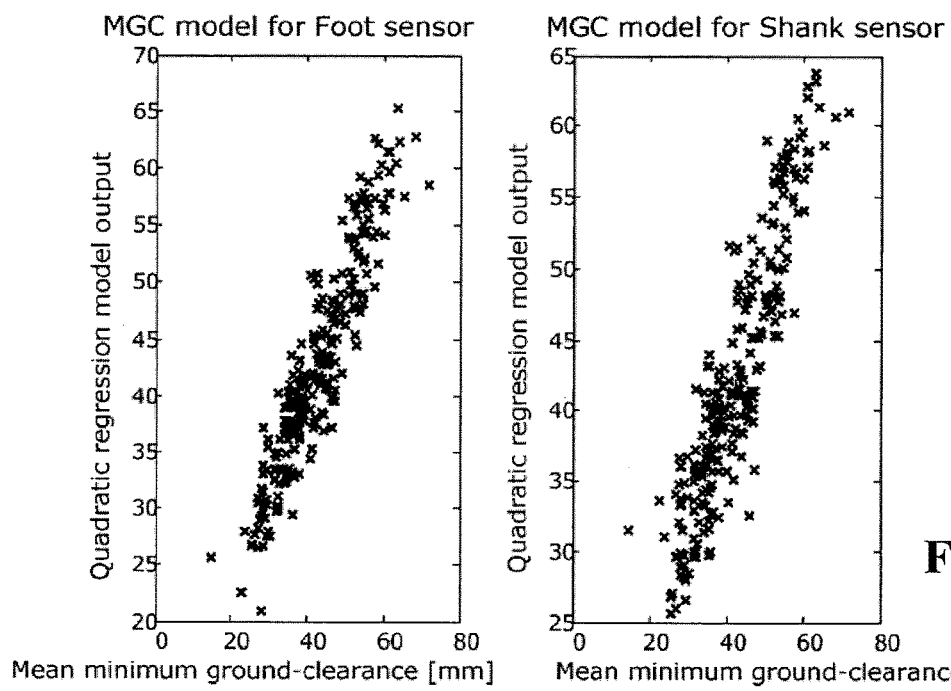
FIG. 7D illustrates example outputs of a quadratic regression model of a MGC parameter.

FIG. 5 illustrates example linear regression lines for the mean MGC of nine individuals. In this example, separate linear regression lines may be generated, one set for inertial parameters from sensors mounted on the left feet of the individuals and one set for inertial sensors mounted on the right feet. One or more of the regression lines may be used as a linear regression to predict the MGC in other individuals. For example, a regression line derived from a walking trial done by participant #4 may be used to calculate subsequent MGC's of participant #4 by collecting subsequent inertial sensor data from him or her. The regression line may also be used to calculate the MGC from the inertial sensor data of an individual or individuals with similar age, weight, shank length, height, gait speed, and/or other physical characteristics to participant #4. For example, FIG. 6A shows an example relationship between an individual's weight and the slope of the regression line for that individual, while FIG. 6B shows an example relationship between an individual's shank length (e.g., the length between the individual's knee and ankle) and the slope of the regression line for that individual. The MGC for an individual may be calculated from a regression line that has a slope that best corresponds to the individual's weight and shank length.

In one embodiment, regression lines derived from a group of individuals with similar age, weight, shank length, height, gait speed, and/or other physical characteristics may be averaged. The average regression line may be used to calculate future MGC values for one of those individuals, or for another individual having characteristics similar to that of the group.

Other regression models, such as quadratic, interaction, and stepwise interaction regression models may be generated. Table 1 shows example $R^2$ values of example regression models based on data collected by a foot-mounted inertial sensor and example regression models based on data collected by a shank-mounted inertial sensor.

TABLE 1

| Model | Foot | Shank |
| --- | --- | --- |
| Linear | 0.66 | 0.60 |
| Interaction | 0.85 | 0.82 |
| Stepwise Interaction | 0.83 | 0.80 |
| Quadratic | 0.85 | 0.82 |

FIGS. 7A-D illustrate how MGC calculations made by these regression models compare against reference MGC values measured by, for example, an optical motion capture system. FIGS. 7A-D illustrate MGC calculations produced from a linear, interaction, stepwise interaction regression, and quadratic regression models, respectively. Separate regression models may be generated for inertial sensor data collected from different body parts. For example, a regression model may be generated from data collected by a foot-mounted inertial sensor, and another regression model may be generated from data collected by a shank-mounted inertial sensor. Separate regression models may be generated for different sides of the body. For example, a regression model may be generated from data collected from an inertial sensor mounted on a left foot of a body, and another regression model may be generated from data collected from an inertial sensor mounted on a right foot of the body. The type of regression model, such as linear, quadratic, interaction, and stepwise interaction, may be selected based on which type of regression model yields the best $R^2$ value (representing proportion of variability in the data explained by the model).

Figure 8:
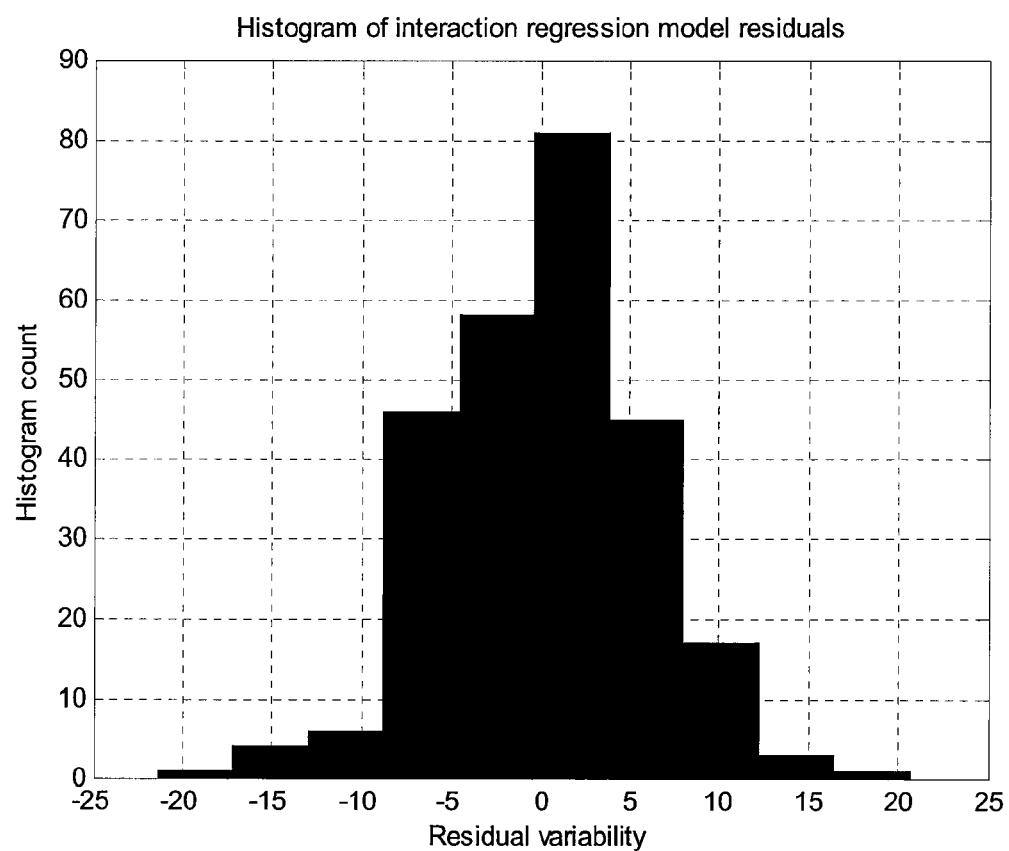
FIG. 8 illustrates example residual variability in regression models.

FIG. 8 illustrates an example histogram of residuals from an interaction regression model derived from data collected by a foot-mounted inertial sensor. The histogram of residuals may be used to evaluate whether a regression model is a good fit for the inertial sensor data. For example, a normal distribution of the model's residuals may indicate that it is a good fit for the data.

The inertial sensor data from the walking trial may also be directly correlated with a risk of falling. For example, shank angular velocity measurements in the sagittal plane (SagAngVel) and parameters derived from those measurements for fallers and non-fallers may be compared. Gait velocity may also be measured from the faller and non-faller participants and may also be compared. A walking trial participant from whom inertial sensor data is collected may be asked for his or her falls history.

Figure 9:
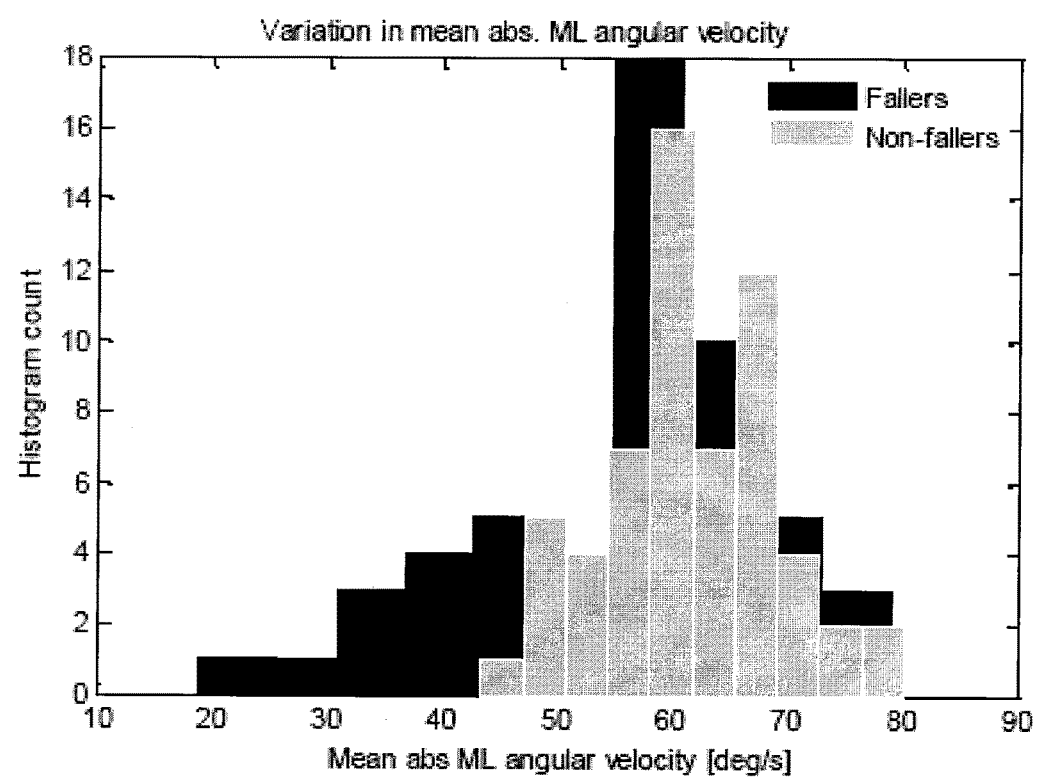
FIG. 9 illustrates an example histogram illustrating angular velocity measurements among fallers and non-fallers.

Inertial sensor parameters that may be compared include, for example, the SagAngVel measurements as well as mean absolute value, maximum, minimum, mean value at mid-swing points, and coefficient of variation of the SagAngVel measurements. FIG. 9, for example, illustrates an example histogram showing the relationship between the number of fallers and non-fallers in a test population and the mean absolute value medio-lateral shank angular velocity (gyroscope Y-axis) measured from those fallers and non-fallers.

The Mann-Whitney version of the Wilcoxon rank sum may be used to test for significant differences between fallers and non-fallers with respect to their gait velocities and derived SagAngVel parameters, especially for SagAngVel parameters that have shown association with the mean and CV MGC.

Further, the SagAngVel parameters may be compared against two other parameters that measure falls risk: BBS score and TUG time. The BBS and TUG tests may be conducted contemporaneously with the walking trial in which the inertial sensor data was collected. For example, during the walking trial in which inertial sensor data is collected, the participant may also be asked to conduct a TUG test by standing up from a seat, walking 3 to 5 m, turning around, walking back to the seat, and sitting down. The time taken to complete the TUG test (i.e., the TUG time) may be recorded. A Pearson's correlation coefficient may be calculated between a SagAngVel parameter and a TUG time or BBS score to examine the strength of the relationship between them. The Pearson's correlation coefficient may also be calculated between a gait velocity and the TUG time or BBS score to examine the strength of their relationship.

For example, mean SagAngVel at mid-swing points, mean absolute valued SagAngVel, and min SagAngVel may be used to assess the falls risk of the person from whom the angular velocity data was collected. Those three parameters may have statistical characteristics that are different for fallers versus non-fallers, and/or may have a good correlation with measured BBS scores or TUG times. Table I below shows example angular velocity parameters, how they compare between fallers and non-fallers, and their correlation with the BBS score and TUG time.

TABLE II

| Variable | Faller (mean ± std) | Non-faller (mean ± std) | Correlation with BBS (r) | Correlation with TUG (r) |
|---|---|---|---|---|
| Mean Angular velocity at mid-swing point | 167.16 ± 29.63 | 182.28 ± 19.93 | 0.58 | −0.63 |
| Mean absolute valued angular velocity | 56.10 ± 12.26 | 61.60 ± 7.54 | 0.57 | −0.60 |
| Minimum angular velocity | −125.28 ± 24.94 | −136.11 ± 21.99 | −0.44 | 0.53 |
| Maximum angular velocity | 199.01 ± 33.16 | 211.91 ± 29.46 | 0.41 | −0.49 |
| CV Angular Velocity | 84.82 ± 13.04 | 82.35 ± 5.52 | −0.25 | 0.21 |

A Pearson Correlation Coefficient may be calculated between the inertial sensor parameters and gait velocity. Example Pearson Correlation coefficients (r) of the example angular velocity parameters with gait velocity are shown in Table III:

TABLE III

| | R | $R^2$ |
|---|---|---|
| Mean SagAngVel at mid-swing | 0.48 | 0.23 |
| Min SagAngVel | −0.41 | 0.17 |
| Mean absolute value of SagAngVel | 0.40 | 0.16 |
| Max SagAngVel | 0.30 | 0.09 |
| CV SagAngVel | −0.08 | 0.01 |

Comparing the inertial sensor parameters between fallers versus non-fallers and correlating them with other falls risk parameters, such as standard clinical measures like BBS score or TUG time, may identify inertial sensor parameters that distinguish fallers and non-fallers. The inertial sensor parameters may be used as a measure of falls risk, and may be more preferable than the standard clinical measures because the inertial sensor parameters may capture information about a faller that is not captured in other standard measures. For example, a combination of mean absolute valued shank angular velocity, minimum shank angular velocity, and mean shank angular velocity at mid-swing points may be used as a measure of falls risk.

By comparing the inertial sensor parameters between fallers and non-fallers, differences in swing mechanics that may lead to a higher risk of falling may be isolated. The example data above, for instance, may indicate that fallers may have a decreased overall mean absolute-valued angular velocity of the shank segment, along with a decreased mean angular velocity at mid-swing and decreased overall minimum angular velocity. Decreased shank angular velocity may indicate a limitation in lower limb mobility, and may be associated with aging.

The operations described above may be implemented in executable software as a set of logic instructions stored in a machine- or computer-readable medium of a memory such as random access memory (RAM), read only memory (ROM), programmable ROM (PROM), firmware, flash memory, etc., in fixed-functionality hardware using circuit technology such as application specific integrated circuit (ASIC), complementary metal oxide semiconductor (CMOS) or transistor-transistor logic (TTL) technology, or any combination thereof. For example, computer program code to carry out operations may be written in any combination of one or more programming languages, including an object oriented programming language such as Java, Smalltalk, C++ or the like and conventional procedural programming languages, such as the "C" programming language or similar programming languages.

Figure 10:
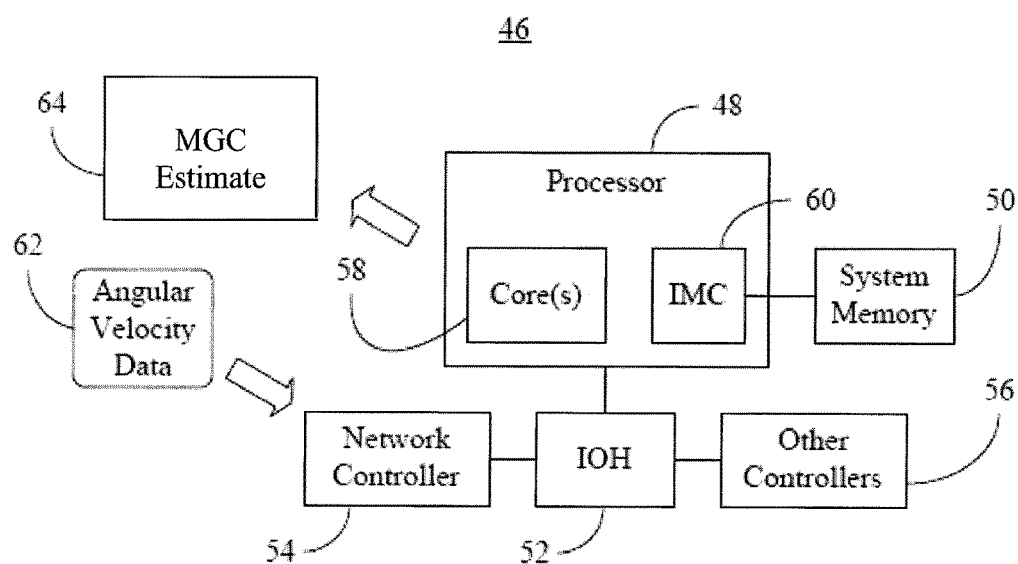
FIG. 10 illustrates an example system for collecting inertial sensor data.

Turning now to FIG. 10, a computing system 46 is shown having a processor 48, system memory 50, an input/output hub (IOH) 52, a network controller 54, and various other controllers 56. The system 46 could be part of a mobile platform such as a laptop, personal digital assistant (PDA), mobile Internet device (MID), wireless smart phone, media player, imaging device, etc., or any combination thereof. For example, the system 46 might be implemented in a wireless smart phone carried by an individual performing a gait assessment in a primary care, community care or home setting. In addition, the system 46 may also be part of a fixed platform such as a personal computer (PC), server, workstation, etc. Thus, the processor 48 may include one or more processor cores 58 capable of running a falls assessment program, frailty assessment program, gait assessment program, or other software with instructions stored in the system memory 50. The system memory 50 could include dynamic random access memory (DRAM) configured as a memory module such as a dual inline memory module (DIMM), a small outline DIMM (SODIMM), etc.

The illustrated IOH 52, sometimes referred to as a Southbridge of a chipset, functions as a host device and communicates with the network controller 54, which could provide off-platform communication functionality for a wide variety of purposes such as cellular telephone (e.g., W-CDMA (UMTS), CDMA2000 (IS-856/IS-2000), etc.), WiFi (e.g., IEEE 802.11, 1999 Edition, LAN/MAN Wireless LANS), Low-Rate Wireless PAN (e.g., IEEE 802.15.4-2006, LR- WPAN), Bluetooth (e.g., IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), and other radio frequency (RF) telephony purposes. In the illustrated example, the network controller 54 obtains angular velocity data 62 wirelessly (e.g., from a data aggregator over a Bluetooth connection), and provides the angular velocity data 62 to the processor 48 for further analysis. The illustrated processor 48 calculates MGC 64 and other parameters and may generate a falls risk assessment.

The other controllers 56 could communicate with the IOH 52 to provide support for user interface devices such as a display, keypad, mouse, etc. in order to allow a user to interact with and perceive information from the system 46.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

I claim:

1. A method for assessing falls risk in one or more persons using a system comprising one or more inertial sensors and at least one processor, the method comprising:
   collecting reference data to generate a regression model using the at least one processor, and wherein the collecting of reference data comprises:
      measuring inertial sensor trial data using one or more inertial sensors on one or more persons during a walking trial; and
      measuring reference minimum ground clearance measurements associated with the one or more persons using an optical motion capture system having at least one camera during the walking trial;
   generating, by the at least one processor, the regression model using: (a) the measured inertial sensor trial data from one or more inertial sensors associated with one or more persons and (b) the measured reference minimum ground clearance measurements from the optical capture system associated with the one or more persons collected as the reference data during the walking trial, wherein the generated regression model represents minimum ground clearance parameters as a function of one or more parameters of the motion data from the one or more inertial sensors;
   after generating the regression model,
   measuring subsequent motion data using one or more inertial sensors on a first person while walking;
   calculating, by the at least one processor, a minimum ground clearance parameter of the first person using the generated regression model, wherein an input to the generated regression model comprises parameters selected from the measured subsequent motion data of the first person, and wherein the calculation is performed without use of data from the optical motion capture system; and
   generating, using the processor, a value indicative of a risk of fall for the first person based on the calculated minimum ground clearance parameter of the first person.

2. The method of claim 1, wherein the minimum ground clearance parameter comprises a mean minimum ground clearance, a coefficient of variation of minimum ground clearance, or any combination thereof.

3. The method of claim 1, wherein the one or more inertial sensors comprise an accelerometer and a gyroscope.

4. The method of claim 1, further comprising one or more foot-mounted inertial sensors for measuring the measured inertial sensor trial data and the measured subsequent motion data of the first person.

5. The method of claim 3, further comprising calculating a mean of absolute values of vertical angular velocity, a mean of absolute values of vertical acceleration, or any combination thereof from the parameters of the measured subsequent motion data, and wherein the calculating the minimum ground clearance parameter of the first person is based on the calculated mean of absolute values of vertical angular velocity and based on the mean of absolute values of vertical acceleration.

6. The method of claim 3, wherein the calculating the minimum ground clearance parameter of the first person is based on a mean angular velocity at a mid-swing point, a minimum angular velocity, a maximum angular velocity, a coefficient of variation of angular velocity, or any combination thereof.

7. The method of claim 1, wherein the generated regression model is a quadratic regression model, an interaction regression model, or any combination thereof.

8. The method of claim 1, wherein the generated regression model is a linear regression model.

9. The method of claim 8, wherein a slope of a regression line derived from the linear regression model is based on the person's weight, shank length, age, or any combination thereof.

10. The method of claim 1, further comprising generating a classifier model of falls risk based on the calculated minimum ground clearance parameter.

11. A non-transitory computer-readable medium, the computer-readable medium comprising one or more instructions that, when executed by one or more processors, cause the one or more processors to perform a method for assessing falls risk in one or more persons, the processors being configured to:
collect data to generate a regression model, wherein the collecting of reference data comprises:
measuring inertial sensor trial data using one or more inertial sensors on one or more persons during a walking trial; and
measuring reference minimum ground clearance measurements associated with the one or more persons using an optical motion capture system having at least one camera during the walking trial;
generate a regression model using: (a) the measured inertial sensor trial data from one or more inertial sensors associated with one or more persons and (b) the measured reference minimum ground clearance measurements from the optical capture system associated with the one or more persons collected as the reference data during the walking trial, wherein the regression model represents minimum ground clearance parameters as a function of one or more parameters of the motion data from the one or more inertial sensors; and, after generating the regression model,
measuring subsequent motion data using one or more inertial sensors on a first person while walking;
calculate, using the generated regression model, a minimum ground clearance parameter of the first person, wherein an input to the regression model comprises parameters selected from the measured subsequent motion data of the first person, and wherein the calculation is performed without use of the optical motion capture system; and
generate a value indicative of a risk of fall for the first person based on the calculated minimum ground clearance parameter of the first person.

12. The non-transitory computer-readable medium of claim 11, wherein the parameters of the measured subsequent motion data comprises angular velocity, mean of the absolute values of angular velocity, maximum angular velocity, minimum angular velocity, coefficient of variation of angular velocity, or any combination thereof.

13. The non-transitory computer-readable medium of claim 12, wherein the selected parameters of the measured subsequent motion data comprises acceleration, mean of the absolute values of acceleration, maximum acceleration, minimum acceleration, coefficient of variation of acceleration, or any combination thereof.

14. The non-transitory computer-readable medium of claim 11, further comprising the processor configured to: receive a second set of selected parameters of measured subsequent motion data using one or more inertial sensors; and
calculate a second set of minimum ground clearance data based on the second set of motion data and the generated regression model.

15. The method of claim 1, wherein the measured inertial sensor trial data comprises inertial sensor data from a left limb of the one or more persons and inertial sensor data from a right limb of the one or more persons, and
wherein the method further comprises: generating, by the processor, separate regression models for the right limb of the one or more persons and for the left limb of the one or more persons, and
wherein the parameters of measured subsequent motion data for the first person input to the regression model comprises inertial sensor data from a left limb and a right limb of the first person.

16. A system for assessing falls risk in one or more persons comprising:
one or more inertial sensors mounted on a body of a first person configured to measure motion data; and
a processor configured to:
collect data to generate a regression model, wherein the collecting of reference data comprises:
measuring inertial sensor trial data using one or more inertial sensors on one or more persons during a walking trial; and
measuring reference minimum ground clearance measurements associated with the one or more persons using an optical motion capture system having at least one camera during the walking trial;
generate a regression model using: (a) the measured inertial sensor trial data from one or more inertial sensors associated with one or more persons and (b) the measured reference minimum ground clearance measurements from the optical capture system associated with the one or more persons collected as the reference data during the walking trial, wherein the regression model represents minimum ground clearance parameters as a function of one or more parameters of the motion data from the one or more inertial sensors; thereafter,
measure subsequent motion data using one or more inertial sensors on a first person while walking;
calculate, using the generated regression model, a minimum ground clearance parameter of the first person, wherein an input to the regression model comprises parameters selected from the measured subsequent motion data of the first person, the motion data associated with the first person being measured using the one or more inertial sensors on the first person, and wherein the calculation is performed without use of the optical motion capture system; and
generate a value indicative of a risk of falling for the first person based on the calculated minimum ground clearance parameter associated with the first person.

17. The method of claim 4, further comprising one or more shank-mounted inertial sensors for measuring the measured inertial sensor trial data and the measured subsequent motion data of the first person.

18. The method of claim 1, further comprising one or more shank-mounted inertial sensors for measuring the measured inertial sensor trial data and the measured subsequent motion data of the first person.

19. The system of claim 16, wherein the measured inertial sensor trial data and the measured subsequent motion data of the first person comprises motion data measured from at least one foot-mounted inertial sensor and at least one shank-mounted inertial sensor.

* * * * *